United States Patent [19]

Goble et al.

[11] Patent Number: 5,571,100

[45] Date of Patent: Nov. 5, 1996

[54] ELECTROSURGICAL APPARATUS

[75] Inventors: Nigel M. Goble, Castleton; Colin C. O. Goble, Penarth, both of Wales

[73] Assignee: Gyrus Medical Limited, Cardiff, Wales

[21] Appl. No.: 331,225

[22] Filed: Oct. 28, 1994

[30] Foreign Application Priority Data

Nov. 1, 1993 [GB] United Kingdom ............ 9322464

[51] Int. Cl.$^6$ .................................................. A61B 17/36
[52] U.S. Cl. ............................... 606/41; 606/45; 606/48; 606/51; 606/52
[58] Field of Search ..................... 606/37–42, 45–52, 606/205–208

[56] References Cited

U.S. PATENT DOCUMENTS

| | | | |
|---|---|---|---|
| 2,113,246 | 4/1938 | Wappler | 606/205 |
| 4,418,692 | 12/1983 | Guay | 606/52 |
| 4,936,842 | 6/1990 | D'Amelio et al. | 606/42 |
| 5,254,117 | 10/1993 | Rigby et al. | 606/46 |
| 5,258,006 | 11/1993 | Rydell et al. | 606/52 |
| 5,322,503 | 6/1994 | Desai | 604/21 |
| 5,334,198 | 8/1994 | Hart et al. | 606/52 |
| 5,342,359 | 8/1994 | Rydell | 606/51 |
| 5,342,381 | 8/1994 | Tidemand | 606/174 |
| 5,342,391 | 8/1994 | Foshee et al. | 606/52 |
| 5,344,428 | 9/1994 | Griffiths | 606/205 |
| 5,360,428 | 11/1994 | Hutchinson, Jr. | 606/46 |

*Primary Examiner*—Angela D. Sykes
*Assistant Examiner*—Michael Peffley
*Attorney, Agent, or Firm*—Fish & Richardson P.C.

[57] ABSTRACT

An electrode assembly for an electrosurgical instrument has an elongate tubular shaft with electrodes mounted on a distal end and, on a proximal end of the shaft, means for detachably mounting the assembly in a handpiece of the instrument. Electrical conductors pass through the shaft from the electrodes to contacts on the mounting means which are located so as to make a connection with a radio frequency source. The mounting means takes the form of a housing shaped for attachment to the handpiece in a non-rotational relationship and, rotatably located within the housing, a sleeve which is fixed to the shaft. The conductors terminate in contact portions secured in the housing of the mounting means and are so formed as to allow the electrodes, the shaft, parts of the conductors in the distal end portions, the shaft, and the sleeve to rotate with respect to the housing and the contact portions about the axis of the shaft.

15 Claims, 2 Drawing Sheets

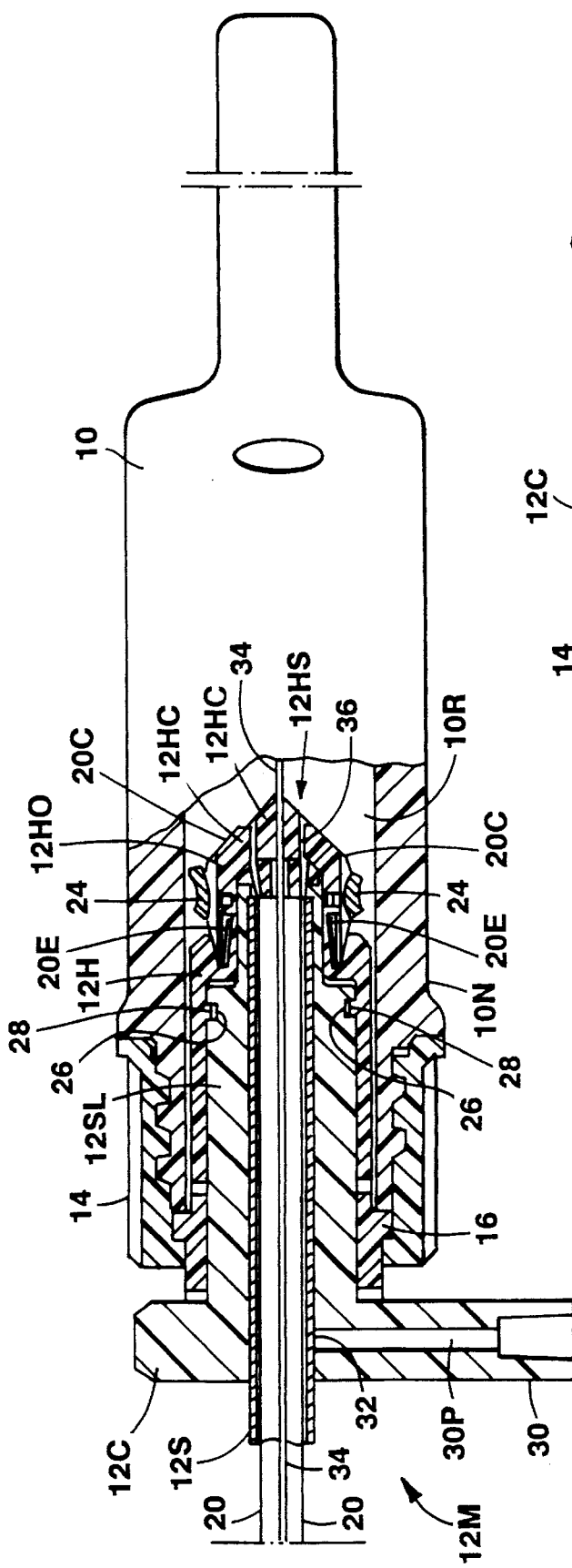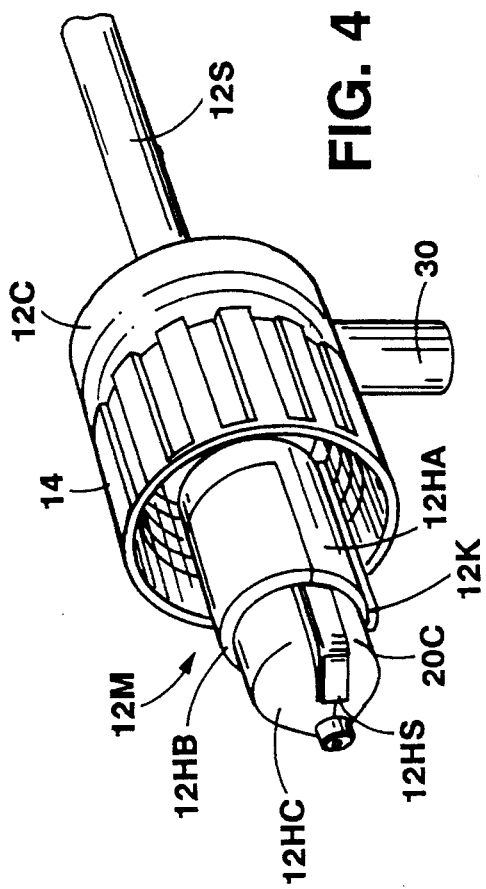

ELECTROSURGICAL APPARATUS

FIELD OF THE INVENTION

This invention relates to an electrosurgical instrument, particularly a laparoscopic instrument, and also to an electrode assembly for such an instrument.

BACKGROUND OF THE INVENTION

It is known to construct an electrosurgical instrument in the form of a handpiece, a tubular shaft mounted in the handpiece and, at a distal end of the shaft, at least one fixed or movable electrode supplied with a radio frequency electrical potential via a conductor passing through the shaft and the handpiece. In an instrument for laparoscopic use in particular, it is advantageous to be able to rotate the electrode or electrodes about the axis of the shaft with respect to the handpiece. In addition, it is conventional to be able to remove and replace electrodes so that new electrodes are used for each surgical procedure. Generally, the remainder of the instrument is sterilisable and can be used for a number (typically 10) of operations before disposal.

SUMMARY OF THE INVENTION

According to this invention, an improved electrode assembly for an electrosurgical instrument comprises an elongate tubular shaft mounting on a distal end portion thereof at least one electrode, an electrical conductor passing through the shaft and connected to the electrode, and, mounted on a proximal end portion of the shaft, mounting means for detachably mounting the assembly in a handpiece of the instrument, the mounting means comprising a first component shaped for attachment to the handpiece in a non-rotational relationship, and a second component secured to the shaft and rotatable with the shaft with respect to the first component about a longitudinal axis of the shaft, the conductor terminating in a contact portion housed in the first component and being so formed as to allow the electrode, the shaft, a part of the conductor in the distal end portion of the shaft, and the second component to rotate with respect to the first component and the contact portion about the longitudinal axis. This allows the assembly to be detachably mounted in the handpiece whilst permitting rotation of the shaft and electrode with respect to the handpiece. Preferably, the or each contact portion is fixed with respect to the first component whereby rotation of the shaft and electrode can be achieved without simultaneous sliding rotational contact between the contact portion and a supply conductor in the handpiece, giving improved reliability. Such an arrangement permits separate sterilisation of the handpiece which can, as a result, be used many more times than is customary with known instruments. In addition, the electrode assembly can be sterilised complete with electrodes, allowing multiple use. Consequently, the cost of electrosurgery can be reduced. Preferably, the conductor is flexible over at least part of its length, and may, indeed, be formed as a single metallic element which is flexible over substantially the whole of the length of the shaft.

For bipolar electrosurgery, the electrode assembly may have two electrodes mounted on the distal end portion of the shaft, and two respective flexible conductors inside the shaft insulated from one another and having two respective contact portions housed in the first component of the mounting means. The conductors may be elongate metallic strips, with each strip being formed from a resilient material such as spring steel with the or each contact portion integral with the respective strip.

The contact portion may be bent back in the distal direction with respect to a portion of the conductor extending through the shaft so as to lie on the outside of the first component of the mounting means for connection to an appropriately positioned contact in the handpiece. In the preferred embodiment of the invention, the second component of the mounting means is a sleeve fixed to the proximal end portion of the shaft, rotation control means being provided on the sleeve. In this case, the first component may comprise a tubular housing for the sleeve.

The tubular housing may include means for securing the end of the or each contact portion, and may have a longitudinal key feature such as a longitudinal key ridge or rail for engaging a corresponding key feature in the handpiece, allowing sliding insertion of the housing into the handpiece when the electrode assembly is being attached to the handpiece, but, at the same time, preventing rotation of the housing with respect to the handpiece. Consequently, the contact portion is held at a fixed rotational position with respect to a mating contact or contacts in the handpiece. A discontinuity may be provided in the form of an annular rail or groove in the interior surface of the housing for locating the sleeve inside longitudinally. Preferably, the housing is in at least two parts, one of the parts comprising a cover, the discontinuity being provided on the cover.

An irrigation fluid passageway in communication with the interior of the shaft may be provided in the second component to allow irrigation fluid to be pumped along the shaft, a flexible seal being situated at the proximal end of the shaft to close off the interior of the shaft at that end.

The invention also includes an electrosurgical instrument comprising a handpiece and an electrode assembly as described above, detachably mounted to the handpiece. The handpiece includes electrical supply conductors, at least one of which has a contact for sliding contact with a contact portion of the electrode assembly.

Electrical connection between the contact portion of the electrode assembly and the handpiece supply conductor contact is best achieved by sliding contact in the longitudinal or axial direction when the electrode assembly is inserted into or removed from the handpiece. Either the contact or the contact portion, or both, may be resiliently deflectable to allow for tolerances in dimensions of the handpiece or the assembly.

The invention will be described below by way of example with reference to the drawings.

BRIEF DESCRIPTION OF THE DRAWINGS

In the drawings:

FIG. 2 is a longitudinally sectioned plan view of a handpiece and a proximal part of the electrode assembly of the instrument of FIG. 1;

FIG. 4 is a perspective view of the proximal part of the electrode assembly.

DETAILED DESCRIPTION OF THE PREFERRED EMBODIMENT

Figure 1:
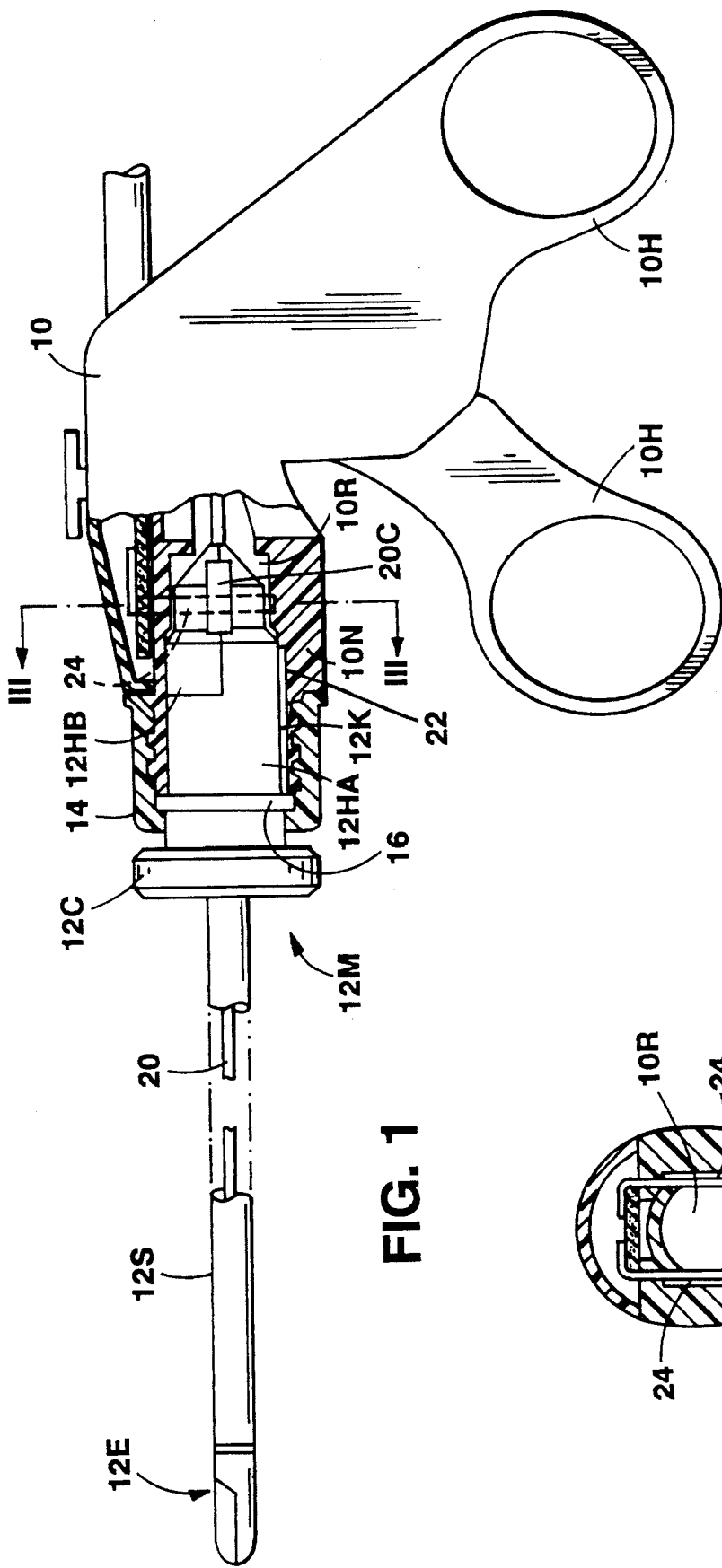
FIG. 1 is a partly sectioned side view of an electrosurgical instrument having an electrode assembly in accordance with the invention.

Referring to FIGS. 1 to 4, a laparoscopic electrosurgical instrument in accordance with the invention has a handpiece 10 with a hollow nose portion 10N providing a receptacle 10R for a detachable electrode assembly 12 which, in FIG. 1, is shown mounted inside the handpiece receptacle 10R.

The electrode assembly comprises mounting means 12M received in the receptacle 10R and held in place by a screw-threaded retaining ring 14 which captures an annular ridge 16 on the outer surface of the mounting means 12M, the retaining ring being screw-threaded onto the outer cylindrical surface of the handpiece nose 10N.

The electrode assembly further comprises a tubular stainless steel shaft 12S, the proximal end portion of which is secured inside the mounting means 12M and, mounted on the distal end of the shaft 12S is a pair of electrodes 12E for bipolar electrosurgical cautery, for example.

Figure 3:
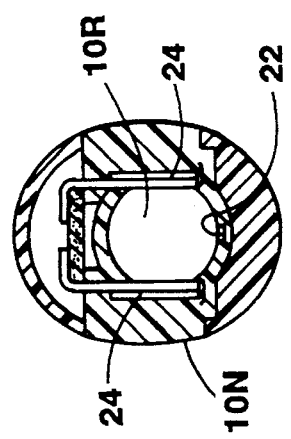
FIG. 3 is a transverse cross-section through the handpiece on the line III—III in FIG. 1.

Running through the tubular shaft 12S is a pair of flexible electrical conductors 20, each of which extends from a respective electrode 12E to an integral spring steel contact portion 20C located on the outer surface of the mounting means 12M. In fact, the contact portions 20C are mounted on diametrically opposite sides of the mounting means 12M, and a longitudinal key rail 12K is integrally moulded on a lower surface of the mounting means 12M for engaging a keyway 22 in the receptacle 10R of the handpiece 10, this keyway being visible in the transverse cross-section of the handpiece nose in FIG. 3. Due to upper positioning of the keyway 22, the contacts 20C, which are perpendicularly arranged with respect to the key rail 12K on the mounting means 12M, are received on opposite sides of the receptacle 10R where they engage vertically oriented metallic contact posts 24 housed in the handpiece nose 10N, as shown in FIGS. 2 and 3. Supply conductors (not shown) inside the handpiece 10 connect the contact posts 24 to a source of radio frequency electrical power.

the construction of the electrode assembly mounting means 12M allows the electrodes 12E, together with the tubular shaft 12S, to be rotated about the axis of the shaft relative to the handpiece 10 without disturbing the relative locations of the contact portions 20C and the contact posts 24.

Referring to FIG. 2, the mounting means 12M have two main components. A first component comprises a tubular housing 12H, in the form of an elongate cap, which receives the second component constituted by a sleeve 12SL surrounding, and fixed to, the proximal end portion of the tubular shaft 12S. Both components are plastic mouldings, the sleeve 12SL being rotatable inside the housing 12H about the longitudinal axis of the shaft 12S, and having an annular groove 26 which receives an interior annular ridge 28 of the housing 12H to provide longitudinal location of the sleeve 12SL within the housing 12H. Since the sleeve 12SL is fixed to the shaft 12S, and since, as described above, the housing 12H is so mounted in the handpiece nose 10N that it cannot rotate with respect to the handpiece 10, rotation of the sleeve 12SL causes rotation of the shaft 12S and electrodes 12E with respect to the handpiece 10 about the axis of the shaft 12S. A collar portion 12C of the sleeve 12SL, visible in FIGS. 1, 2, and 4, is exposed beyond the end of the handpiece nose 10N when the electrode assembly 12 is mounted in the handpiece 10, where it can be gripped for rotating the electrodes 12E, as required, during use.

Incorporated in the rotation collar 12C is an integral pipe stub 30 (see FIG. 2) with an inner passageway 30P in registry with an aperture 32 in the tubular shaft 12S to allow the supply of irrigation fluid to the interior of the tubular shaft 12S and thence to the region of the electrodes 12E.

Referring to FIG. 4 in conjunction with FIG. 1, the housing of the mounting means 12M is in two parts, the first part 12HA constituting the main part of the housing 12H extends the full length of the housing and includes the whole of the rotation collar 12C. In the region of the end of the mounting means 12M furthest from the electrodes, the main part 12HA is in the form of a half cylinder, the other half of the cylinder being formed by the second part 12HB acting as a cover which is a snap fit on the main part 12HA. As will be seen by comparing FIGS. 1 and 2, the annular ridge 28 for locating the sleeve 12SL is formed at a location where the main part 12HA and the cover part 12HB of the housing 12H form opposite walls of the housing 12M, so that part of the ridge 28 is formed by a feature of the cover part 12HB. This allows assembly of the mounting means 12M by placement of the sleeve 12SL within the main part 12HA of the housing 12H, followed by snap location of the cover part 12HB to secure the sleeve 12SL with its locating groove 26 housing the ridge 28, as shown in FIG. 2.

Referring to FIGS. 1, 3 and 4, the electrical conductors 20 connected to the electrodes 12E are formed as stainless steel strips each with an insulative coating (not shown) to isolate the conductors from the shaft 12S and a control rod 34 passing through the shaft 12S for controlling movement of the electrodes 12E. At the end of the shaft 12S which is furthest from the electrodes 12E, the conductors pass through an elastomeric sealing cap 36 (e.g. made of silicone rubber) which is clamped over the end of the sleeve 12SL by the housing 12H to seal off the interior space of the proximal end portion of the tubular shaft 12S thereby to prevent escape of irrigation fluid supplied via passage 30P. This clamping is effected by the cap configuration of the housing 12H which has a generally conical cap end 12HC for guiding the electrode assembly into its receptacle in handpiece 10. As mentioned above, the contact portions 20C are arranged on the outside of the housing 12H in diametrically opposite positions, as shown in FIG. 4. In fact, the contact portions 20C are integral parts of the conductors 20, the metallic strip in each case being exposed to the outside of the housing 12H insofar as the end portion of each conductor 20, here without an insulating covering, passes through a respective slot or aperture 12HS in the end cap of the housing 12H and is bent back in the distal direction over the outer surface of the housing 12H, the extreme end portion 20E of each strip being folded inwardly to run once again in the proximal direction in a cavity in the housing 12H, thereby securing the exposed contact portion 20C. By referring to FIG. 4, it will be appreciated that the slots 12HS and the cavities housing the extreme end portions 20E of the conductors are formed in both parts 12HA and 12HB of the housing.

Each contact portion 20C is formed so that it stands away from the outer surface 12HO of the housing 12H over a portion of its length so as to be resiliently deflectable towards the surface 12HO by the contact posts 24 (see FIGS. 2 and 3) when the electrode assembly is inserted in the handpiece receptacle 10R.

The control rod 34 for the electrodes passes through the sealing cap 36 and the cap end of the housing 12H to be received within the handpiece 10.

It will now be appreciated that, to prepare the instrument for use, the electrode assembly 12, sterilised, is mounted in the handpiece 10 by pushing the mounting means 12M (FIG. 1), with the retaining ring 14 in place around the annular ridge 16, into the receptacle 10R with the contact portions 20C facing opposite sides of the handpiece 10 so that the guide rail 12K engage the keyway 22 in the handpiece nose 10N. When the mounting means 12M is pushed fully home in the receptacle 10R, the contact posts 24 of the handpiece engage the contact portions 20C of the electrode assembly to form an electrical circuit between the supply conductors in the handpiece and the electrodes 12E. The assembly is secured in the handpiece by screwing the retaining ring 14 onto the threaded external surface of the handpiece nose 10N, as shown in FIG. 2. Since the sleeve part 12SL of the mounting means 12M is rotatable within the housing part 12H, but is fixed to the tubular shaft 12S, rotation of the rotation collar 12C causes the electrodes 12E also to rotate, allowing the surgeon to orient the electrodes as required while keeping the handpiece in the most suitable orientation for manipulating the instrument, and operating the handles 10H. Since the conductors 20 are free to move inside the tubular shaft 12S, the electrodes 12E may be rotated about the axis of the shaft without rotation of the contact portions 20C. Consequently, no rotational sliding contact between the contact portions 20C and the contact posts 24 in the handpiece is necessary, with a consequent improved reliability of connection.

What is claimed is:

1. An electrode assembly for an electrosurgical instrument, the assembly comprising an elongate tubular shaft mounting on a distal end portion thereof at least one electrode, an electrical conductor passing through the shaft and connected to the electrode, and, mounted on a proximal end portion of the shaft, mounting means for detachably mounting the assembly to a handpiece of the instrument, the mounting means comprising a first component shaped for attachment to the handpiece in a non-rotational relationship, and a second component rotatably coupled to the first component and secured to the shaft and rotatable with the shaft with respect to the first component about a longitudinal axis of the shaft, the conductor terminating in a contact portion housed in the first component and being formed so as to allow the electrode, the shaft, a part of the conductor in the distal end portion of the shaft, and the second component to rotate with respect to the first component and the contact portion about the longitudinal axis.

2. An assembly according to claim 1, having two electrodes mounted on the distal end portion of the shaft, and two respective insulated conductors inside the shaft insulated from one another and having two respective contact portions housed in the first component of the mounting means.

3. An assembly according to claim 1, wherein the conductor is formed as an elongate metallic strip.

4. An assembly according to claim 3, wherein the contact portion is integral with the strip.

5. An assembly according to claim 3, wherein the contact portion is bent back in the distal direction with respect to a portion of the conductor extending through the shaft.

6. An assembly according to claim 1, wherein the second component comprises a sleeve fixed to the proximal end portion of the shaft and rotation control means on the sleeve, and the first component comprises a tubular housing for the sleeve.

7. An assembly according to claim 6, wherein the tubular housing includes means for securing the end of the contact portion.

8. An assembly according to claim 6, wherein the tubular housing includes a key feature for allowing slidable insertion of the housing into the handpiece but preventing rotation with respect to the handpiece.

9. An assembly according to claim 6, wherein the tubular housing has a discontinuity for longitudinal location of the housing with respect to the second component.

10. An assembly according to claim 9, wherein the housing has a cover and the discontinuity is on the cover.

11. An assembly according to claim 6, wherein the second component includes an irrigation fluid passageway in communication with the interior of the shaft and wherein the assembly includes a flexible seal arranged to close the interior of the distal end portion of the shaft.

12. An electrosurgical instrument comprising a handpiece and an electrode assembly detachably mounted to the handpiece, wherein the electrode assembly comprises an elongate tubular shaft mounting on a distal end portion thereof at least one electrode, an electrical conductor passing through the shaft and connected to the electrode, and, mounted on a proximal end portion of the shaft, mounting means for detachably mounting the assembly to a handpiece of the instrument, the mounting means comprising a first component shaped for attachment to the handpiece in a non-rotational relationship, and a second component rotatably coupled to the first component and secured to the shaft and rotatable with the shaft with respect to the first component about a longitudinal axis of the shaft, the conductor terminating in a contact portion housed in the first component and being formed so as to allow the electrode, the shaft, a part of the conductor in the distal end portion of the shaft, and the second component to rotate with respect to the first component and the contact portion about the longitudinal axis, and wherein the handpiece includes electrical supply conductors at least one of which has a contact for sliding contact with said contact portion of the assembly.

13. An instrument according to claim 12, wherein the handpiece supply conductor contact and the electrode assembly contact portion are arranged for relative sliding contact with each other in an axial direction, one of (a) the handpiece contact and (b) the electrode assembly contact portion being resiliently deflectable.

14. An electrode assembly for an electrosurgical instrument, the assembly comprising an elongate tubular shaft mounting on a distal end portion thereof a plurality of electrodes, a plurality of corresponding electrical conductors passing through the shaft and connected to the electrodes, and, mounted on a proximal end portion of the shaft, mounting means for detachably mounting the assembly to a handpiece of the instrument, the mounting means comprising a first component shaped for attachment to the handpiece in a non-rotational relationship, and a second component rotatably coupled to the first component and secured to the shaft and rotatable with the shaft with respect to the first component about a longitudinal axis of the shaft, the conductors terminating in a plurality of corresponding contact portions housed in the first component and being formed so as to allow the electrodes, the shaft, a part of each conductor in the distal end portion of the shaft, and the second component to rotate with respect to the first component and the contact portions about the longitudinal axis.

15. An electrosurgical instrument comprising a handpiece and an electrode assembly detachably mounted to the handpiece, wherein the electrode assembly comprises an elongate tubular shaft mounting on a distal end portion thereof a plurality of electrodes, a plurality of corresponding electrical conductors passing through the shaft and connected to the electrodes, and, mounted on a proximal end portion of the shaft, mounting means for detachably mounting the assembly to a handpiece of the instrument, the mounting means comprising a first component shaped for attachment to the handpiece in a non-rotational relationship, and a second component rotatably coupled to the first component and secured to the shaft and rotatable with the shaft with respect to the first component about a longitudinal axis of the shaft, the conductors terminating in a plurality of corresponding contact portions housed in the first component and being formed so as to allow the electrodes, the shaft, a part of each conductor in the distal end portion of the shaft, and the second component to rotate with respect to the first component and the contact portions about the longitudinal axis, and wherein the handpiece includes a plurality of electrical supply conductors each contacting a corresponding contact portion of the assembly.

* * * * *

REEXAMINATION CERTIFICATE (3415th)
United States Patent [19]
Goble et al.

[11] B1 5,571,100
[45] Certificate Issued Jan. 6, 1998

[54] ELECTROSURGICAL APPARATUS

[75] Inventors: Nigel M. Goble, Castleton; Colin C. O. Goble, Penarth, both of Wales

[73] Assignee: Gyrus Medical Limited, St. Mellons, Wales

Reexamination Request:
No. 90/004,517, Jan. 14, 1997

Reexamination Certificate for:
Patent No.: 5,571,100
Issued: Nov. 5, 1996
Appl. No.: 331,225
Filed: Oct. 28, 1994

[30] Foreign Application Priority Data

Nov. 1, 1993 [GB] United Kingdom ............ 9322464

[51] Int. Cl.$^6$ .............................................. A61B 17/36
[52] U.S. Cl. ............................... 606/41; 606/45; 606/48; 606/51; 606/52
[58] Field of Search .................. 606/37–42, 45–52, 606/205–208

[56] References Cited

U.S. PATENT DOCUMENTS

| | | | |
|---|---|---|---|
| 4,003,380 | 1/1977 | Wien | 606/51 |
| 4,823,791 | 4/1989 | D'Amelio | 606/45 |
| 5,133,713 | 7/1992 | Huang et al. | 606/46 |
| 5,257,990 | 11/1993 | Nash | 606/45 |
| 5,282,806 | 2/1994 | Haber et al. | 606/139 |
| 5,352,235 | 10/1994 | Koros et al. | 606/174 |
| 5,391,166 | 2/1995 | Eggers | 606/48 |
| 5,395,312 | 3/1995 | Desai | 604/22 |
| 5,433,725 | 7/1995 | Christian et al. | 606/207 |
| 5,478,351 | 12/1995 | Meade et al. | 606/205 |
| 5,499,992 | 3/1996 | Meade et al. | 606/170 |

OTHER PUBLICATIONS

Karl Storz Endoscopy America (insert to product brochure) "Dissecting and Grasping Forceps Take–Apart–Rotating", Karl Storz GmbH Mar. 1993.

"Mediflex Surgical Products" Product Brochure, Islandia, New York.

"System III, Rotating Laparoscopic Instruments", Leisegang Product Brochure, Leisegang Medical Inc. Boca Rotan, Florida.

*Primary Examiner*—Michael Peffley

[57] ABSTRACT

An electrode assembly for an electrosurgical instrument has an elongate tubular shaft with electrodes mounted on a distal end and, on a proximal end of the shaft, means for detachably mounting the assembly in a handpiece of the instrument. Electrical conductors pass throgh the shaft from the electrodes to contacts on the mounting means which are located so as to make a connection with a radio frequency source. The mounting means takes the form of a housing shaped for attachment to the handpiece in a non-rotational relationship and, rotatably located within the housing, a sleeve which is fixed to the shaft. The conductors terminate in contact portions secured in the housing of the mounting means and are so formed as to allow the electrodes, the shaft, parts of the conductors in the distal end portions, the shaft, and the sleeve to rotate with respect to the housing and the contact portions about the axis of the shaft.

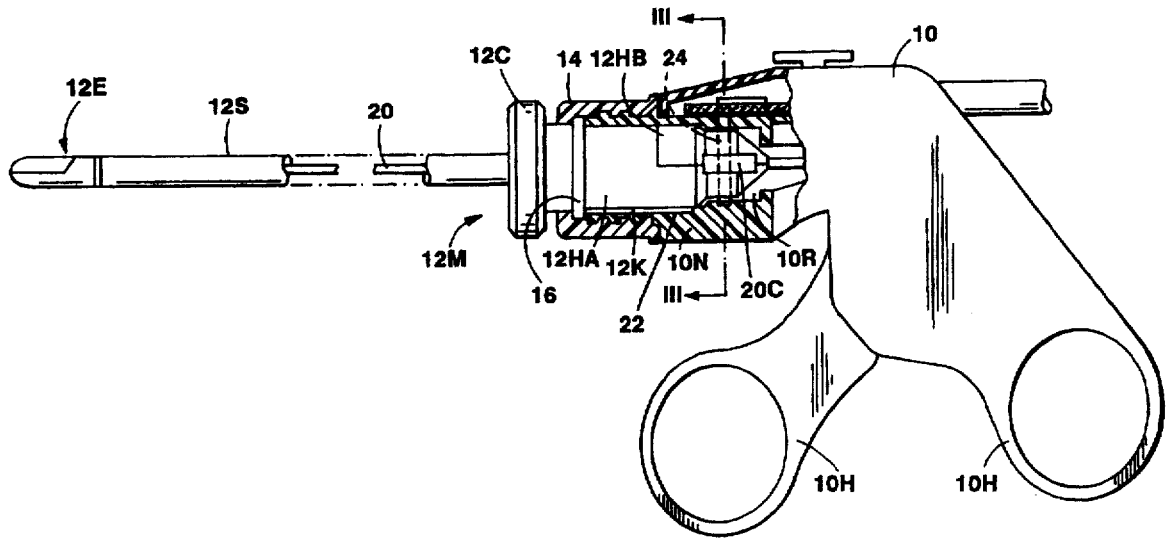

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *